(12) United States Patent
Wada et al.

(10) Patent No.: US 10,546,239 B2
(45) Date of Patent: Jan. 28, 2020

(54) CAUSAL NETWORK GENERATION SYSTEM AND DATA STRUCTURE FOR CAUSAL RELATIONSHIP

(71) Applicant: OMRON Corporation, Kyoto-shi, Kyoto (JP)

(72) Inventors: Hirotaka Wada, Nara (JP); Keiichi Obayashi, Nara (JP); Ayako Kokubo, Uji (JP)

(73) Assignee: OMRON Corporation, Kyoto-shi (JP)

( * ) Notice: Subject to any disclaimer, the term of this patent is extended or adjusted under 35 U.S.C. 154(b) by 732 days.

(21) Appl. No.: 15/115,105

(22) PCT Filed: Feb. 6, 2015

(86) PCT No.: PCT/JP2015/053336
§ 371 (c)(1),
(2) Date: Jul. 28, 2016

(87) PCT Pub. No.: WO2015/122362
PCT Pub. Date: Aug. 20, 2015

(65) Prior Publication Data
US 2017/0220937 A1     Aug. 3, 2017

(30) Foreign Application Priority Data

Feb. 14, 2014   (JP) .................... 2014-026160

(51) Int. Cl.
*G06N 5/04* (2006.01)
*G16H 50/20* (2018.01)
*G06F 16/22* (2019.01)

(52) U.S. Cl.
CPC .......... *G06N 5/04* (2013.01); *G06F 16/2228* (2019.01); *G16H 50/20* (2018.01)

(58) Field of Classification Search
CPC .......... G06N 5/04; G06N 5/025; G16H 50/20; G06F 16/2228; G06F 17/18; G06F 19/3481; G06K 9/00
See application file for complete search history.

(56) References Cited

U.S. PATENT DOCUMENTS

| 5,528,516 A | 6/1996 | Yemini et al. |
| 6,063,028 A * | 5/2000 | Luciano ................. G16H 50/50 600/300 |

(Continued)

FOREIGN PATENT DOCUMENTS

| EP | 0760939 B1 | 10/2001 |
| JP | S62-053760 B2 | 11/1987 |

(Continued)

OTHER PUBLICATIONS

Kazuki Komura et al., "Analysis of the influence networks among stock indexes by using Transfer Entropy", The Japanese Society for Artificial Intelligence Kenkyukai Shiryo, Jan. 22, 2014, pp. 22 to 27, SIG-FIN-012-06, Cited in the ISR.

(Continued)

*Primary Examiner* — Kamran Afshar
*Assistant Examiner* — Imad Kassim
(74) *Attorney, Agent, or Firm* — Metrolex IP Law Group, PLLC

(57) ABSTRACT

A causal relationship is represented with a data structure including target identification information for identifying a target, index identification information of each of indexes to be used for quantitatively describing an event that occurs in the target, and causal relationship information for each pair of two indexes selected from the indexes. The causal relationship information includes direction information representing which one of the two indexes is a cause index and which one is an effect index, strength information representing a causal strength between the cause index and the effect (Continued)

index, time information representing a delay time for propagation of an influence of the cause index to the effect index, and correlation information representing a direction of change in the effect index with respect to an increase or decrease in the cause index.

4 Claims, 17 Drawing Sheets

(56) References Cited

U.S. PATENT DOCUMENTS

| | | | | |
|---|---|---|---|---|
| 2010/0332439 A1* | 12/2010 | Adachi | ............... | G06Q 30/02 |
| | | | | 706/52 |
| 2011/0201902 A1* | 8/2011 | Shiga | ............. | G06F 19/00 |
| | | | | 600/300 |
| 2012/0136629 A1* | 5/2012 | Tamaki | .............. | G05B 23/0254 |
| | | | | 702/183 |
| 2016/0362305 A1* | 12/2016 | Ohtsuki | ............. | G05B 13/0205 |

FOREIGN PATENT DOCUMENTS

| | | |
|---|---|---|
| JP | H05-333186 A | 12/1993 |
| JP | H08-234832 A | 9/1996 |
| JP | 2008-242887 A | 10/2008 |
| JP | 2012-113537 A | 6/2012 |

OTHER PUBLICATIONS

Extended European search report dated Jun. 13, 2017 in the counterpart European patent application.

* cited by examiner

CAUSAL NETWORK GENERATION SYSTEM AND DATA STRUCTURE FOR CAUSAL RELATIONSHIP

TECHNICAL FIELD

The present invention relates to a technique of generating a causal network and a data structure for a causal relationship.

BACKGROUND ART

A method has been conventionally known in which causal relationships (called a causal network) among a plurality of events (elements) are represented by a table or graph for use in predicting the behavior in a complex system or deducing the cause of a problem occurring in the system. For example, in a Bayesian network, each element is treated as a random variable, and a causal relationship between elements is represented by a conditional probability. PTL 1 discloses an example of using a causal-loop diagram (CLD) in risk assessment of a software development project. In the causal-loop diagram, the notation is such that elements having a causal relationship are connected with an arc, the arc being added with a plus sign in the case of a positive correlation, a minus sign in the case of a negative correlation, or double lines in the case where there is a time delay until the effect appears. PTL 2 discloses an example in which, in the case where an abnormality has occurred in a large-scale plant, a cause-and-effect table associating an assumed cause of abnormality with an indication pattern of each surveillance index is referenced to identify the cause. PTL 3 discloses an example of preparing a causal network defining the order and interval of alarms to be generated by an interlock system upon occurrence of an abnormality in a large-scale plant, so that, when an alarm is actually generated, an operator can predict an alarm that is possibly generated next and measures to be taken in response thereto. PTL 4 shows a multi-layer causal network in which causal graphs (graphs in which elements having a positive correlation are connected with a "plus" arc and elements having a negative correlation are connected with a "minus" arc) for respective elapsed times t1, t2, and so forth are arranged in the order of time to represent changes in causal relationships among elements over time since the occurrence of an abnormality.

CITATION LIST

Patent Literature

PTL 1: Japanese Patent Application Laid-open No. 2012-113537
PTL 2: Japanese Patent Application Laid-open No. H8-234832
PTL 3: Japanese Patent Application Laid-open No. H5-333186
PTL 4: Japanese Examined Patent Publication No. S62-53760

SUMMARY OF INVENTION

Technical Problem

In order to accurately perform an analysis or prediction of the behavior of a target, it is important to understand the causal propagation, i.e., when and how the occurrence of an event A influences another event B. However, in conventional causal networks, the propagation strength and propagation delay (time delay) in cause and effect have not been successfully modeled, and there has been a problem that a complex causal relationship a target has cannot be represented sufficiently.

The present invention has been made in view of the above circumstance, and an object is to provide a technique for representing clearly the behavior of a target having a complex causal relationship involving a time delay.

Solution to Problem

The invention is a data structure for a causal relationship, including target identification information for identifying a target for which a causal relationship is represented, index identification information of each of a plurality of indexes used for quantitatively describing an event that occurs to the target, and causal relationship information for each pair of two different indexes selected from the plurality of indexes, the causal relationship information including direction information representing which one of the two indexes is a cause index and which one is an effect index, strength information representing a causal strength between the cause index and the effect index, time information representing a delay time for propagation of an influence of the cause index to the effect index, and correlation information representing a direction of change in the effect index with respect to an increase or decrease in the cause index. With the invention, the behavior of the target having a complex causal relationship involving a time delay can be represented accurately.

The invention is the data structure for a causal relationship, wherein the strength information represents a causal strength between a change in the cause index and a change in the effect index after a delay time represented by the time information. With the invention, the causal strength in consideration of a propagation delay from the cause index to the effect index can be represented.

The invention is the data structure for a causal relationship, wherein the time information represents a delay time with which the causal strength between the cause index and the effect index becomes maximum, and the strength information represents a maximum causal strength between the cause index and the effect index. With the invention, the causal strength in consideration of a propagation delay from the cause index to the effect index can be represented. The difference in causal strength or difference in delay time for each combination of indexes can also be represented clearly.

The invention is the data structure for a causal relationship, wherein the time information includes information of n delay times from first to n-th (where n is an integer greater than or equal to 2), and the strength information includes information of n causal strengths corresponding to the respective first to n-th delay times. With the invention, the causal strength in consideration of a propagation delay from the cause index to the effect index can be represented. The difference in causal strength or difference in delay time for each combination of indexes and further the change in causal strength for each delay time can also be represented clearly.

The invention is the data structure for a causal relationship, wherein the correlation information represents a correlation coefficient between a value of the cause index and a value of the effect index after a delay time represented by the time information. With the invention, the strength of correlation can be represented clearly, in addition to the direction of change in the effect index with respect to the increase/decrease in the cause index (whether the correlation is positive or the correlation is negative).

The invention is a causal network generation system to generate a causal network representing a causal relationship between a plurality of events that occur to a target, the causal network generation system including a data acquisition unit that acquires time series data of each of a plurality of indexes used for quantitatively describing the plurality of events, a causal relationship evaluation unit that evaluates, for each pair of two different indexes selected from the plurality of indexes, a causal relationship between the two indexes, and an output unit that outputs data describing a causal relationship for each pair of the two indexes evaluated by the causal relationship evaluation unit, the causal relationship evaluation unit assuming one of the two indexes as a cause index and the other as an effect index, and calculating a causal strength between a change in the cause index and a change in the effect index after a time s while varying a value of the time s to evaluate a causal strength between the cause index and the effect index and a delay time for propagation of an influence of the cause index to the effect index. With the invention, the causal network representing clearly the behavior of the target having a complex causal relationship involving a time delay can be generated.

The invention is the causal network generation system, wherein the causal relationship evaluation unit evaluates a delay time with which the causal strength between the cause index and the effect index becomes maximum, and the causal relationship output from the output unit includes information of the delay time with which the causal strength between the cause index and the effect index becomes maximum and information of a maximum causal strength between the cause index and the effect index. With the invention, the causal network representing the causal strength in consideration of a propagation delay from the cause index to the effect index can be generated.

The invention is the causal network generation system, wherein the causal relationship evaluation unit evaluates the causal strength between the cause index and the effect index for n delay times from first to n-th (where n is an integer greater than or equal to 2), and the causal relationship output from the output unit includes information of n delay times from first to n-th and information of n causal strengths corresponding to the respective first to n-th delay times. With the invention, the causal network representing the causal strength in consideration of a propagation delay from the cause index to the effect index can be generated. The causal network also representing clearly the difference in causal strength or difference in delay time for each combination of indexes can be generated.

The invention is the causal network generation system, wherein the causal relationship evaluation unit calculates a correlation coefficient between a value of the cause index and a value of the effect index after the delay time, and the causal relationship output from the output unit includes information of the correlation coefficient. With the invention, the causal network representing clearly the relationship of an increase/decrease in the cause index and a change in the effect index (whether a correlation is positive or the correlation is negative) and also the strength of correlation can be generated.

The invention is the causal network generation system, wherein the causal relationship evaluation unit evaluates a causal strength between the cause index and the effect index using transfer entropy. With the invention, the causal relationship involving a time delay and the causal strength thereof can be evaluated appropriately by using transfer entropy.

Advantageous Effects of Invention

The present invention enables a clear representation of the behavior of a target having a complex causal relationship involving a time delay.

DESCRIPTION OF EMBODIMENTS

<Causal Network Generation System>

A causal network generation system according to an embodiment of the present invention will be described. The causal network generation system is a system for automatically generating a causal network representing causal relationships among a plurality of events that occur to a target of analysis. The causal network is for representing the behavior of a target of analysis, and is applicable to analyses and predictions of behaviors of various targets such as, for example, management and maintenance of a production line or large-scale plant, prediction of weather or a disaster, forecasting of stock prices or currency exchange rates, or marketing.

Figure 1:
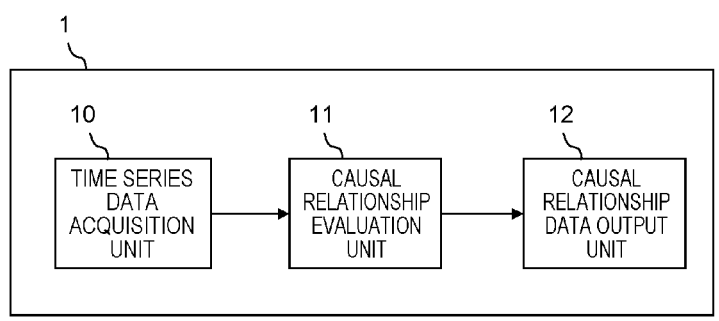
FIG. 1 A functional block diagram of a causal network generation system.

FIG. 1 shows a functional configuration example of a causal network generation system 1. The causal network generation system 1 includes functional blocks such as a time series data acquisition unit 10, a causal relationship evaluation unit 11, and a causal relationship data output unit 12. The system 1 can be configured of a general-purpose computer including a central processing unit (CPU), a primary storage device (memory), an auxiliary storage device (such as a hard disk or semiconductor disk), an input device (such as a keyboard, mouse, or touch panel), a display device (such as a liquid crystal monitor), and a communication IF. Each function shown in FIG. 1 is realized by the CPU reading and executing a program. The system 1 can be configured of one device or can be configured of a plurality of devices capable of wired or wireless communication with each other.

The time series data acquisition unit 10 is a function of acquiring time series data that of an index used for quantitatively describing an event that occurs to a target of analysis. The type and number of events (indexes) can be designed at will to suit the target or purpose of analysis. For example, if the purpose is maintenance of a production line, environmental data such as the output of a sensor provided to a manufacturing device, the manufacturing conditions, the operating time, the rolled throughput yield and first time yield, and the temperature and humidity can be chosen as the indexes. In a complex system, time series data of several tens to several hundreds of types of indexes can be used.

The causal relationship evaluation unit 11 is a function of assessing the causal relationships among respective indexes. As described above, in order to accurately perform an analysis or prediction of the behavior of a target, a correct understanding is necessary of the causal strength between two indexes (a cause index and an effect index) and the delay time for propagation of the influence of the cause index to the effect index. Thus, the causal relationship evaluation unit 11 of this embodiment assesses the causal relationship between two indexes, using the concept of "transfer entropy (TE)" in information theory.

Transfer entropy is a measure or method of assessing a causal relationship in consideration of a propagation time (delay time) between two indexes X and Y. The average amount of information (entropy) that has transferred from index X to index Y after a time s is regarded as the strength (i.e., causal strength) of the influence of the cause index X on the effect index Y after the time s. A correlation coefficient is a similar concept, but a correlation coefficient merely assesses the degree of a linear relationship between two indexes X and Y and the sign of the linear relationship, and differs from transfer entropy in that the direction of cause and effect (which index is the cause and which is the effect) and the time delay are not taken into consideration.

Assuming time series data of respective indexes X and Y as x(t) and y(t) and the probability density function as P(x(t)) and P(y(t)), a transfer entropy $TE_{XY}(s)$ relating to the delay time s, with index X as the cause and index Y as the effect, can be calculated with the following equation.

$$TE_{XY}(s) = \left[\log_2 \frac{P(y(t+s), y(t), x(t)) \cdot P(y(t))}{P(y(t), x(t)) \cdot P(y(t+s), y(t))}\right]$$ [Math. 1]

Herein, P(a,b) represents joint probability density variables of P(a) and P(b), and [*] represents the time average of *.

As can be seen from the above equation, the transfer entropy can be calculated, given the time series data of two indexes X and Y and the delay time s. In the case where a causal relationship such that X is the cause and Y is the effect exists between indexes X and Y, $TE_{XY}(s) > TE_{YX}(s)$ holds between the value of $TE_{XY}(s)$ and the value of $TE_{YX}(s)$ calculated with the cause and effect reversed. Thus, by assessing the magnitude relationship of the values of $TE_{XY}(s)$ and $TE_{YX}(s)$, the existence of the causal relationship and the direction of cause and effect can be determined. By calculating the transfer entropy $TE_{XY}(s)$ while varying the value of s, the maximum value of the causal strength between the cause index X and the effect index Y and the delay time s with which the causal strength becomes maximum can be evaluated.

The causal relationship data output unit 12 is a function that generates and outputs data (referred to as causal relationship data) describing a causal relationship between respective indexes assessed by the causal relationship evaluation unit 11. For the output destination of the causal relationship data, an auxiliary storage device, a display device, a printer, an external storage or computer (on a LAN or the Internet), or the like is assumed.

(Processing of Generating Causal Network)

Figure 2:
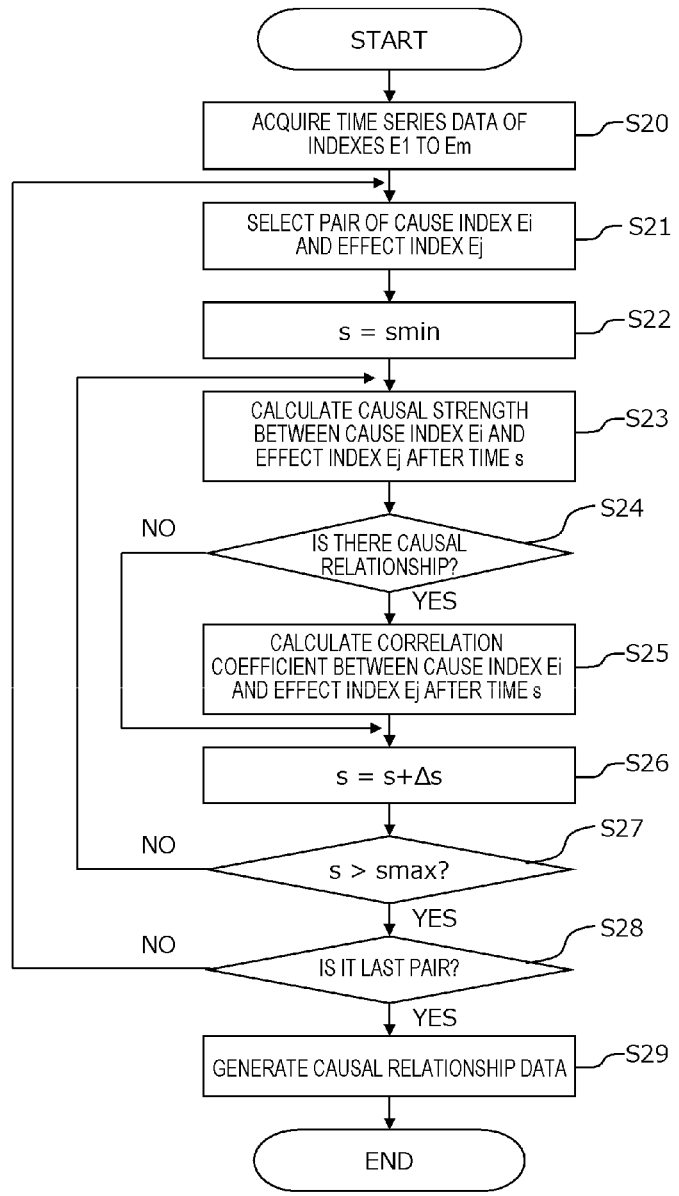
FIG. 2 A flowchart showing the flow of causal network generation processing.

The flow of causal network generation processing by the causal network generation system 1 will be described, along a flowchart in FIG. 2.

Figure 3:
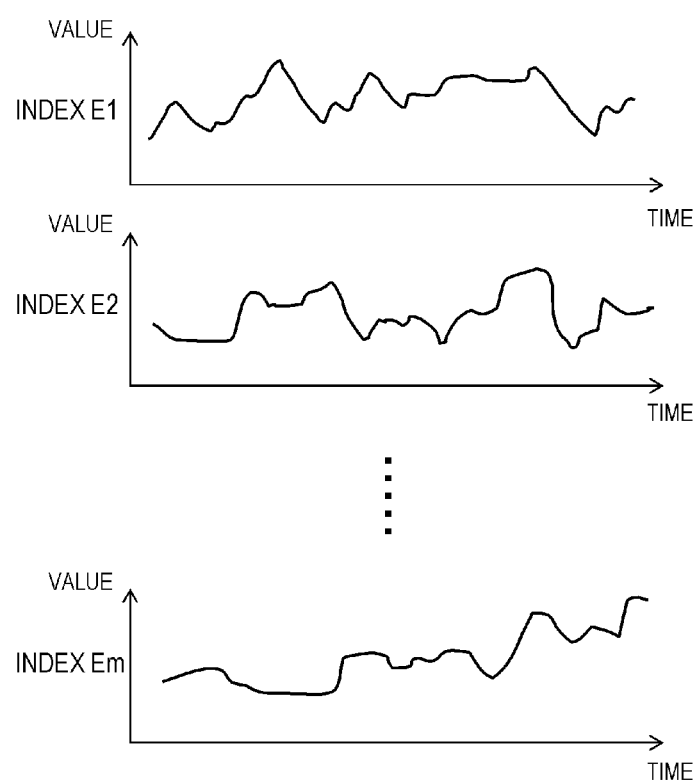
FIG. 3 An example of time series data used in generating a causal network.

In step S20, the time series data acquisition unit 10 acquires time series data of a plurality of indexes relating to a target of analysis. Herein, it is assumed that time series data of m indexes E1 to Em (where m is an integer greater than or equal to 2) is acquired. The source of acquisition and method of acquisition of the time series data are not limited. For example, data stored in an auxiliary storage device may be read, or data may be acquired from an external storage device or computer via a LAN or the Internet. FIG. 3 schematically shows an example of the time series data. The abscissa of each graph is the time axis, and the ordinate is the value of the index.

Subsequently, the causal relationship evaluation unit 11 performs the following processing for each pair of two indexes (Ei and Ej) selected from the m indexes E1 to Em (step S21). Herein, Ei represents the cause index, and Ej the effect index. Indices i and j representing the index number satisfy i equals 1 to m, j equals 1 to m, and i≠j.

First, the causal relationship evaluation unit 11 sets the delay time s to a minimum value smin (step S22). Then, the causal relationship evaluation unit 11 evaluates the causal strength between the cause index Ei and the effect index Ej after the time s (step S23). In this embodiment, a transfer entropy TEij calculated with the formula above is used as the causal strength. In the case where the transfer entropy in the opposite direction, i.e., a transfer entropy TEji from index Ej to index Ei after the time s, is calculated and the transfer entropy in the opposite direction is greater (TEji>TEij), it is advisable to determine that a causal relationship such that index Ei is the cause and index Ej is the effect is absent between the two indexes (Ei and Ej) and assume the causal strength as 0.

In the case where a causal relationship between the cause index Ei and the effect index Ej is recognized (in the case where the causal strength is not 0) (YES in step S24), the causal relationship evaluation unit 11 calculates the correlation coefficient of the cause index Ei and the effect index Ej after the time s (step S25). The method of calculating the correlation coefficient is known, and therefore description is omitted.

The processing of steps S23 to S25 above is executed repeatedly while increasing the value of s by a time step width Δs (step S26). When the processing has ended for up to a maximum value smax of the delay time (step S27), it proceeds to the processing for the next pair of indexes (NO in step S28). When the evaluation of a causal relationship has ended for all possible pairs of two indexes (YES in step S28), the causal relationship data output unit 12 generates causal relationship data (step S29) and ends the processing.

<Data Structure for Causal Relationship>

Figure 4:
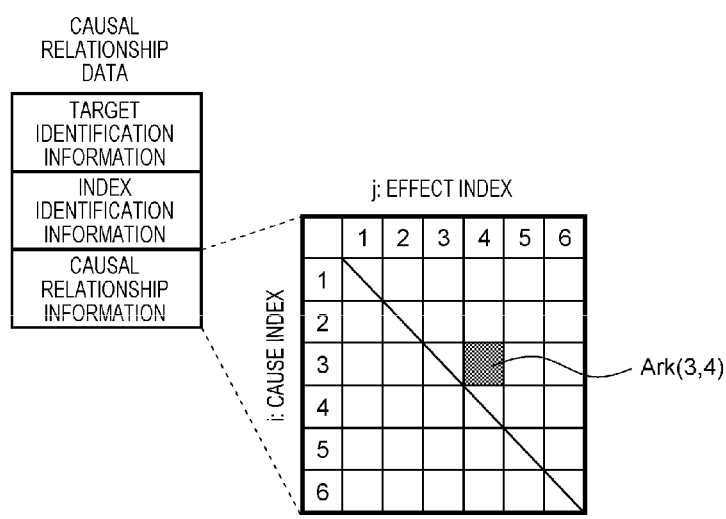
FIG. 4 An example of a data structure of causal relationship data.

FIG. 4 schematically shows an example of a data structure of causal relationship data. The causal relationship data includes target identification information for identifying a target (target of analysis) for which a causal relationship is represented, index identification information of each of m indexes, and causal relationship information for each pair of two indexes.

The target identification information describes the name, the ID, or the like of the target of analysis. The target identification information is information to be referenced in order to identify what the causal relationship represented by the causal relationship data pertains to, and thus may describe any content as long as distinction from other targets of analysis can be made. The index identification information describes the name, the ID, or the like for identifying an index or event. The index identification information is information to be referenced in order to identify what each index represents, and thus may describe any content as long as distinction from other indexes can be made.

The causal relationship information is configured of a two-dimensional array of m×m (where m=6 in the example of FIG. 4), and causal relationship information between a cause index i and an effect index j is stored in a cell of element number (i,j). An example of data description of causal relationship information Ark(3,4) for element number (3,4) is shown below.

```
Ark (3, 4) = {
    Causality = 0.58;
    Delay = 3;
    Co_CoEf = −0.7
}
```

Causality is strength information representing the maximum causal strength (transfer entropy) between the cause index i and the effect index j, and Delay is time information representing the delay time with which the causal strength becomes maximum. Co_CoEf is correlation information representing the direction of change in the effect index j with respect to an increase or decrease in the cause index i (whether the correlation is positive or the correlation is negative). In this example, "day" is used as units for Delay, and the correlation coefficient between the cause index i and the effect index j after Delay is used as the correlation information. That is, from the causal relationship information Ark(3,4) in the above example, it can be seen that a causal relationship exists between a cause index 3 and an effect index 4 with the direction of cause and effect being from index 3 to index 4, the causal strength is 0.58, it takes (there is a delay of) 3 days for the influence of the cause index 3 to propagate to the index 4, there is a negative correlation between the cause index 3 and the effect index 4, and the strength thereof is 0.7.

In the case where it is determined that a causal relationship is absent between indexes i and j in step S24 described above, NULL is set for Ark(i,j). NULL is also set for cells of Ark(i,j) where i=j.

The causal relationship information may describe information of the causal strength and correlation coefficient corresponding to each of n delay times from first to n-th (where n is an integer greater than or equal to 2), instead of describing only the maximum value of the causal strength and the delay time and correlation coefficient at the time. An example of data description of the causal relationship information Ark(3,4) for element number (3,4) is shown below.

```
Ark (3, 4) = {
    Causality [ ] = {0.02, 0.13, 3.2, . . . };
    Co_CoEf [ ] = {−0.2, −0.13, −0.7, . . . }
}
```

In this description example, data of strength information (Causality[ ]) and correlation information (Co_CoEf[ ]) is held in a one-dimensional array. The element number of the array corresponds to the delay time (in units of "days"). That is, Causality[0]=0.02 represents the causal strength in the case where the delay is 0 days (delay is absent), Causality[1]=0.13 the causal strength in the case where the delay is 1 day, and so forth, and Co_CoEf[0]=−0.2 represents the correlation coefficient in the case where the delay is 0 days, Co_CoEf[1]=−0.13 the correlation coefficient in the case where the delay is 1 day, and so forth. In the case where the units (time step width) of the delay time are to be set at will, an array Delay[ ] of the delay time may be held, as in an example of data description below.

```
Ark (3, 4) = {
    Causality [ ] = {0.02, 0.13, 3.2, . . . };
    Delay [ ] = {0, 2, 5, . . . };
    Co_CoEf [ ] = {−0.2, −0.13, −0.7, . . . }
}
```

Such a data structure enables a clear representation of the behavior of a target having a complex causal relationship involving a time delay. From causal relationships involving a plurality of events (indexes), a pair of events (indexes) having a strong causal relationship can be found easily. Moreover, since the propagation delay of cause and effect can be taken into consideration, a more appropriate understanding of causal relationships is possible compared to with conventional methods. Further, since a correlation coefficient between two events (indexes) is also held, the sign of correlation and the strength of correlation can also be represented. With the presence of such information, searching or narrowing down of a causal relationship with a constraint condition in the sign of correlation or the strength of correlation, for example, can be carried out easily, and it is useful for analysis and prediction of the behavior of a target.

Figure 5:
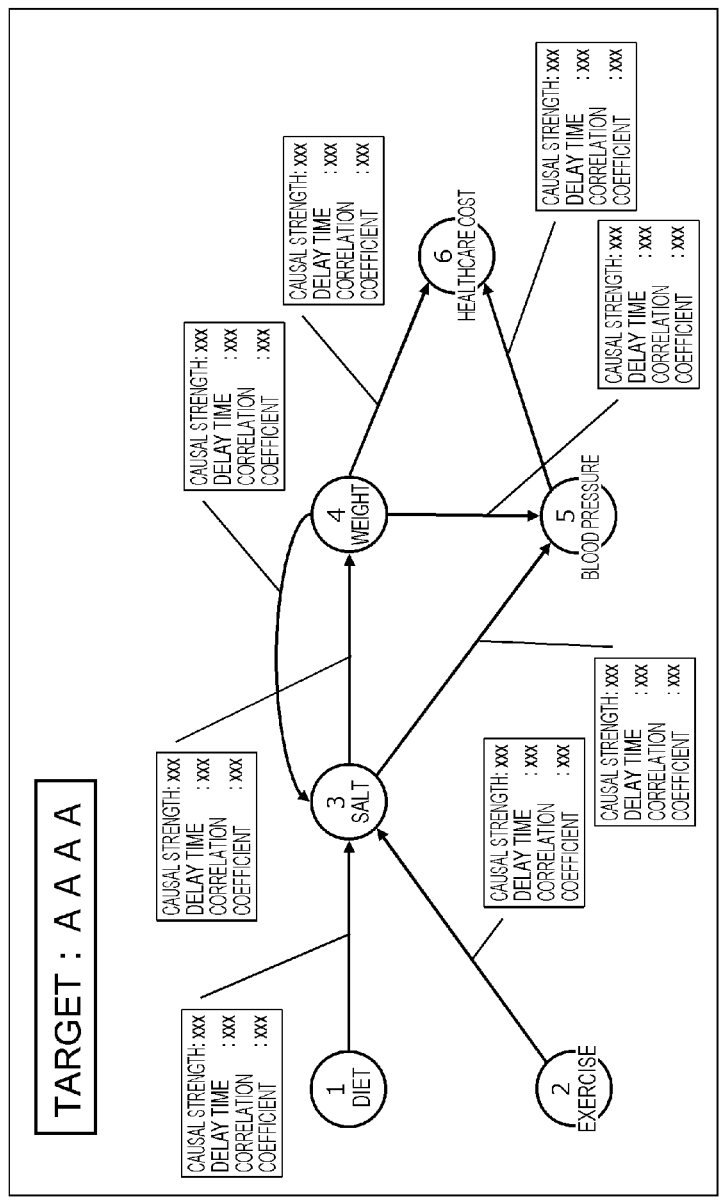
FIG. 5 A display example of a causal network.

FIG. 5 is a display example of a causal network with the causal relationship data output unit 12. In this directed graph, each node corresponds to an index, and an arc that links two nodes shows a causal relationship and the direction of cause and effect between the two nodes (with the base end side of the arc being a cause node and the arrow side being an effect node). The index identification information is displayed for each node, and the causal strength, delay time, and correlation coefficient are displayed for each arc. In the upper portion of the directed graph, the target identification information is displayed. Upon viewing such a causal network, the presence or absence of a causal relationship between indexes, the direction of cause and effect, the causal strength, the time it takes for propagation of cause and effect, the sign and degree of a correlation, and the like can be grasped easily.

In the above processing, a causal relationship has been evaluated from time series data of one target of analysis. However, a causal relationship can be evaluated from time series data of each of a plurality of targets of analysis. For example, analyzing vital data of a plurality of subjects, or analyzing data of a plurality of production lines with the same design can be assumed. Since the basic behavior is common to the same type of targets of analysis, relationships such as the presence or absence of a causal relationship, the direction of cause and effect, the sign of correlation, and the like are supposedly the same. However, there may be individual variability regarding the causal strength and the delay time. In the case of evaluating a causal relationship from time series data of a plurality of targets of analysis, it is advisable to calculate the causal strength, the delay time, the correlation coefficient, or the like for each target of analysis, and further hold the maximum value, the minimum value, the average value, the variance, the standard deviation, or the like thereof as statistic information within causal relationship data. An example of data description of the causal relationship data in such a case is shown below.

```
Ark (3, 4) = {
    Causality [ ] = {2.2, 3.5, 3.0, . . . };
    Causality_Max = 4.4;
    Causality_Ave = 2.8;
    Causality_Var = 0.89;
    Delay [ ] = {3, 2, 4, . . . };
    Delay_Max = 5;
    Delay_Ave = 3.1;
    Delay_Var = 1.88;
    Co_CoEf [ ] = {0.5, 0.32, 0.3, . . . }
}
```

In this description example, data of the strength information (Causality[ ]), time information (Delay[ ]), and correlation information (Co_CoEf[ ]) is held in a one-dimensional array. The element number of an array corresponds to the target-of-analysis number. That is, for the 0-th target of analysis, a causal strength Causality[0] equals 2.2, a delay time Delay[0] equals 3, and a correlation coefficient Co_CoEf[0] equals 0.5. As the statistic information, the maximum value (Causality_Max), average value (Causality_Ave), and variance (Causality_Var) of the causal strength and the maximum value (Delay_Max), average value (Delay_Ave), and variance (Delay_Var) of the delay time are held for all targets of analysis.

Such a data structure enables a clear representation of the behavior of a target (target group), even in the case where there is individual variability in causal strength or propagation delay of cause and effect. Since the statistic information for a plurality of targets is held, there are possibilities of new findings such as, for example, that there is a strong causal relationship between indexes X and Y, but also great individual variability in delay time, or that the reliability for a causal relationship between indexes A and B is low because the dispersion of the causal strength and the dispersion of the delay time for indexes A and B are extremely large.

<Application Example of Causal Network: Health Management Support System>

The causal network (causal relationship data) described above can be applied to an analysis or prediction of the behavior of various targets. As one example, an example of application to a causal analysis of indexes relating to health management of a human will be described below.

In recent years, there has been a growing interest in health, and an increasing number of people are personally keeping records of diets and exercises or recording measured values of vital data, such as the blood pressure or weight, for use in health management. However, even with such information accumulated, it is not easy for a person without expertise in medicine or physiology to find a relationship (causal relationship) between respective numerical values or to gain useful knowledge for health management. Moreover, the way in which vital data changes or the time lag until the influence of a diet or exercise appears as a change in vital data varies from person to person. This is another reason health management is difficult. A health management support system described below is for creating and presenting to a user the causal network described above, so that health management by the user him/herself is made easy.

<System Configuration>

Figure 6:
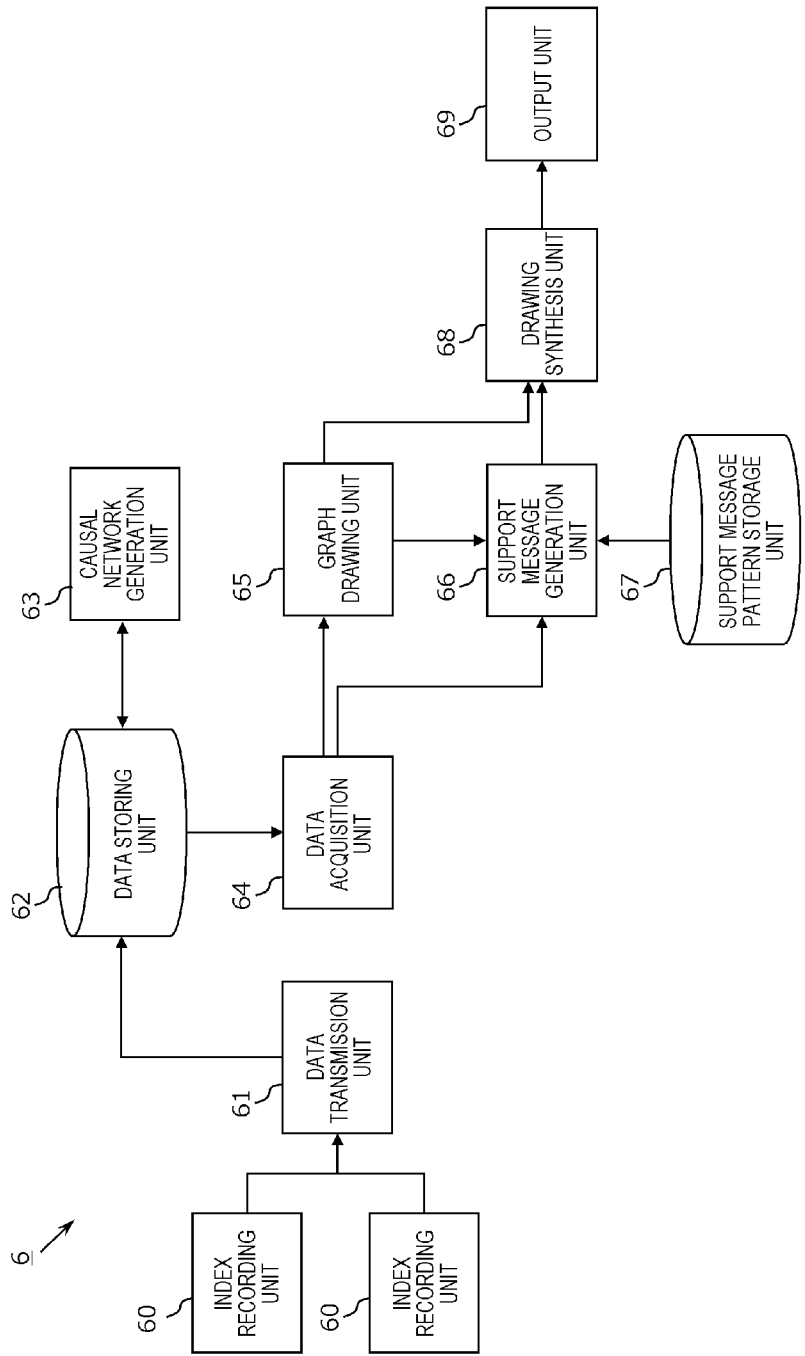
FIG. 6 A functional block diagram of a health management support system.

FIG. 6 is a functional block diagram showing the overall configuration of a health management support system 6 (also referred to simply as "the system 6") according to this embodiment.

The system 6 includes functional blocks such as a plurality of index recording units 60, a data transmission unit 61, a data storing unit 62, a causal network generation unit 63, a data acquisition unit 64, a graph drawing unit 65, a support message generation unit 66, a support message pattern storage unit 67, a drawing synthesis unit 68, and an output unit 69. The functional blocks can be configured of one device or can be configured of a plurality of devices capable of wired or wireless communication with each other. (A specific example of the device configuration will be described later.)

The index recording unit 60 is a functional block that records various indexes that are a measurement or input from a user. Any index relating to health may be recorded. To give an example, the number of steps, walking distance, time of exercise, amount of exercise (calorie consumption), amount of activity (product of the exercise intensity and time), time of sleep, time and number of rests, calorie intake, amount of salt intake, dosage of medicine, and amount of supplement intake are indexes that can influence health, out of activities (motions or actions) carried out by a user. Indicators that are measurements of a user or something collected from a user include the blood pressure, pulse rate, weight, body fat percentage, amount of body fat, muscle percentage, amount of muscle, abdominal circumference, BMI, cholesterol level, blood sugar level, urine sugar level, and body temperature. In addition, the cost or the like of healthcare or medicine can also be treated as an index relating indirectly to health. The configuration may be such that the value of each index is manually input by a user, or it may be such that the index recording unit 60 is configured of a measuring instrument such as a pedometer or blood pressure meter, so that the index value can be measured and recorded automatically.

The data transmission unit 61 is a functional block with which data of each index recorded by the index recording unit 60 is transmitted and registered with respect to the data storing unit 62. The data storing unit 62 is a database that stores and manages data of each index accepted via the data transmission unit 61 in the order of time. Causal relationship data generated by the causal network generation unit 63 is also saved in the data storing unit 62. In the case where the system is used by a plurality of users, data needs to be collected and accumulated for each user. Therefore, it is advisable to manage time series data and causal relationship data of each index together with a user ID for identification of a user.

The causal network generation unit 63 is a block having the same function as the causal network generation system 1 shown in FIG. 1. The causal network generation unit 63 generates causal relationship data from time series data of each index read from the data storing unit 62. The generated causal relationship data is stored in the data storing unit 62.

The data acquisition unit 64 is a functional block that acquires causal relationship data or time series data of an index from the data storing unit 62. The graph drawing unit 65, the support message generation unit 66, the support message pattern storage unit 67, the drawing synthesis unit 68, and the output unit 69 are a group of functional blocks forming an information providing unit that provides a user with support information relating to health management. The graph drawing unit 65 generates a causal network (directed graph) based on causal relationship data or generates a graph of time series data of each index. The support message generation unit 66 performs generation of a support message using a message template registered in the support message pattern storage unit 67, based on causal relationship data or time series data of each index. The generated graph and support message are synthesized by the drawing synthesis unit 68 and output to a display device, an external terminal, or the like by the output unit 69. Specific processing of generating the support information and a specific example of the graph and support message will be described later.

<Example of Device Configuration>

Figure 7A:
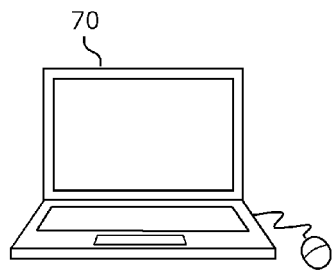
FIG. 7 Configuration examples of the health management support system.
Figure 7B:
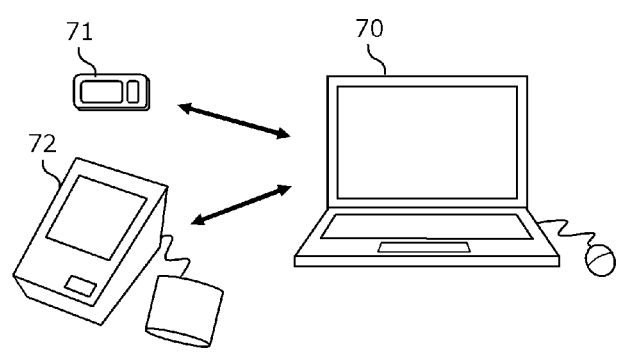

The health management support system in FIG. 6 may employ various device configurations. FIG. 7(*a*) to FIG. 8(*b*) show specific examples of the device configuration.

FIG. 7(*a*) is an example in which the health management support system is configured of one device 70. The device 70 can be configured of a general-purpose personal computer including a central processing unit (CPU), a primary storage device (memory), an auxiliary storage device (such as a hard disk or semiconductor disk), an input device (such as a keyboard, mouse, or touch panel), a display device (such as a liquid crystal monitor), and a communication IF. Alternatively, the device 70 can be configured of a device that provides a function equivalent to that of a personal computer, such as a tablet terminal, smartphone, or personal digital assistant (PDA), or the device 70 can be configured of a dedicated machine with an embedded board computer. In the case of the configuration in FIG. 7(*a*), a user operates the input device to perform data input of each index, and support information is output to the display device.

FIG. 7(*b*) is an example of combining measuring instruments such as a pedometer 71 and a blood pressure meter 72 with the device 70. Data measured with the pedometer 71 or the blood pressure meter 72 is transferred to the device 70 through a wired line (e.g., USB) or wirelessly (e.g., with Bluetooth® or WiFi). In the case of this configuration, the pedometer 71 and the blood pressure meter 72 corresponds to the index recording unit 60 in FIG. 6, and a data communication function embedded in the pedometer 71 and the blood pressure meter 72 corresponds to the data transmission unit 61 in FIG. 6. Support information may be output to the display device of the device 70, or may be transmitted to the pedometer 71 or the blood pressure meter 72 to be output to a display unit of the pedometer 71 and the blood pressure meter 72.

Figure 8A:
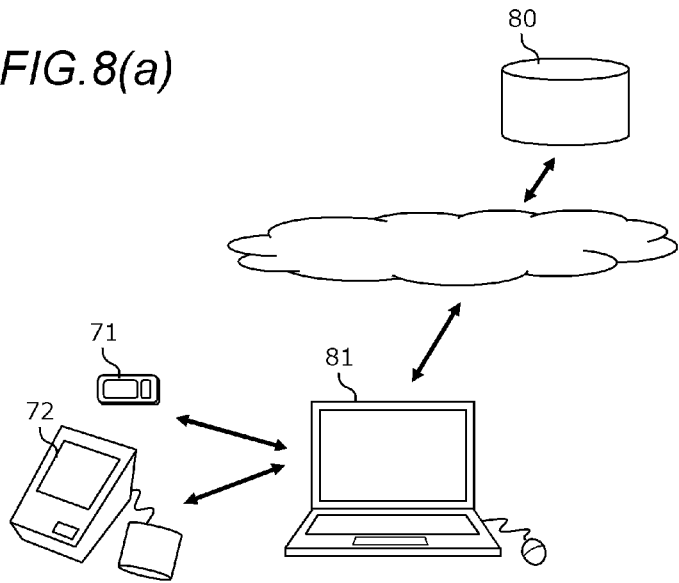
FIG. 8 Configuration examples of the health management support system.
Figure 8B:
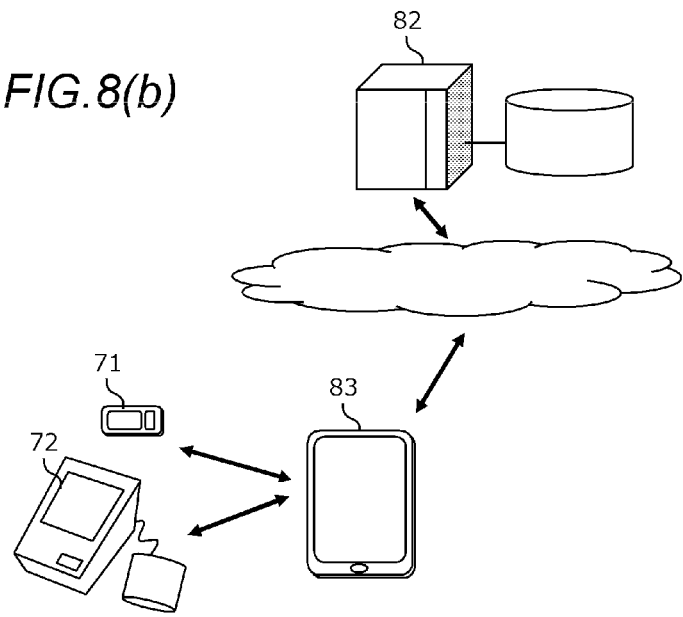

FIG. 8(*a*) is an example of cloud computing and is an example in which the data storing unit 62 in FIG. 6 is configured of an online storage 80. In the configuration of FIG. 8(*a*), a terminal 81 operated by a user includes functions of the data transmission unit 61, the causal network generation unit 63, the data acquisition unit 64, and the information providing unit in FIG. 6, and executes upload of data measured with the pedometer 71 or the blood pressure meter 72, download of time series data, generation of a causal network, generation and display of the support information, and the like. In a similar manner to the device 70 shown in FIG. 7, the terminal 81 can be configured of a personal computer, a tablet terminal, a smartphone, a dedicated machine, or the like. In the case where the pedometer 71 or the blood pressure meter 72 allows for Internet access, data may be uploaded directly to the online storage 80 from the pedometer 71 or the blood pressure meter 72.

FIG. 8(*b*) is also an example of cloud computing. The difference from FIG. 8(*a*) is that a cloud server 82 serves the functions of the data storing unit 62, the causal network generation unit 63, the data acquisition unit 64, and the information providing unit in FIG. 6. On the side of a terminal 83 operated by a user, it suffices to provide a function of a request unit that makes a request for support information with respect to the cloud server 82, a display unit that displays support information received from the cloud server 82, or the like. For identification of a user, it suffices to include a user ID in the request for support information or to perform authentication with the user ID, for example. The configuration of FIG. 8(*b*) can reduce resources (such as the data capacity or computing power) necessary on the terminal side and simplify the configuration of the terminal 83, and therefore is suitable for a service of performing a health management support particularly with an app in a tablet terminal, a smartphone, or the like.

Processing Example 1

An example of processing of analyzing a causal network that is executed by the health management support system 6 will be described. As a premise, it is assumed that a user has, over a certain period (e.g., one month or more), kept a record of six indexes of the diet (calorie intake), exercise (calorie consumption), salt intake, weight, blood pressure, and healthcare cost, and that time series data thereof is already accumulated in the data storing unit 62. It is also assumed that, based on the time series data of the six indexes, the causal network generation unit 63 has generated a causal network (see FIG. 2 for specific processing), and that causal relationship data thereof is already accumulated in the data storing unit 62.

Figure 9:
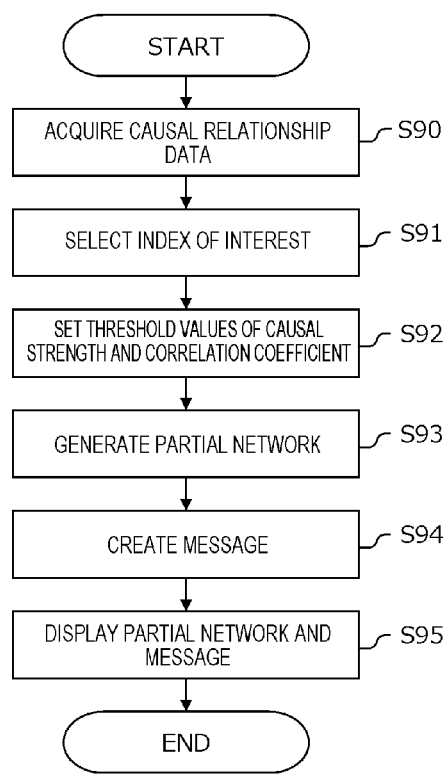
FIG. 9 A flowchart showing the flow of processing of the health management support system.
Figure 10A:
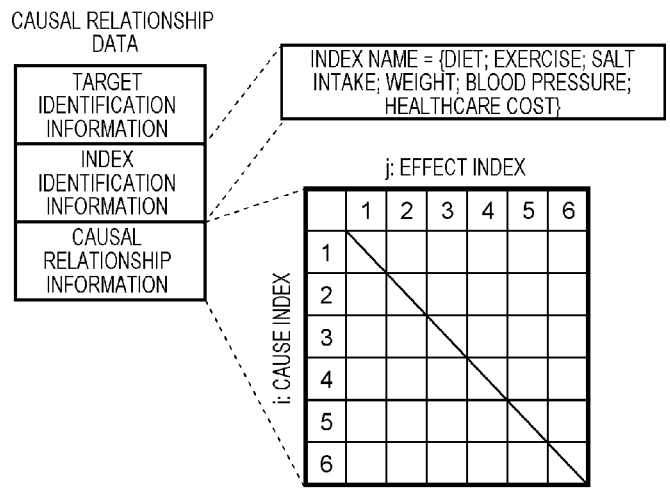
FIG. 10 Examples of causal relationship data, a causal network, and a partial network.
Figure 10B:
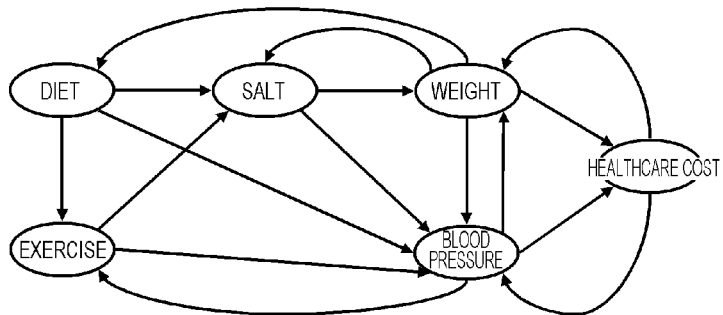
Figure 10C:
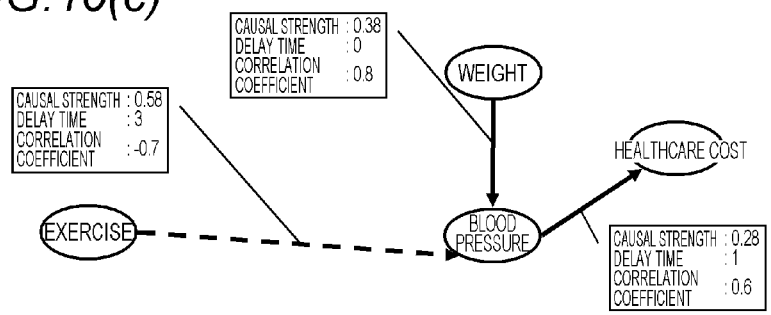

The flow of processing will be described, along a flowchart in FIG. 9. First, the data acquisition unit 64 acquires causal relationship data from the data storing unit 62 (step S90). FIG. 10(*a*) is an example of the causal relationship data, and FIG. 10(*b*) is an example of a causal network (directed graph) drawn based on the causal relationship data. As shown in FIG. 10(*b*), an extremely complex network is generated when causal relationships of all indexes are represented, and it is difficult to figure out the relationships of the indexes and the points to be noted.

The graph drawing unit 65 provides a function of creating a partial network described next. First, the graph drawing unit 65 selects an index of interest from the six indexes (step S91). The index of interest may be either one. For example, a user him/herself may designate an index for which a causal analysis is intended, or the graph drawing unit 65 may select an index to which causal relationships with other indexes are concentrated as the index of interest. Herein, it is assumed that "index 5: blood pressure" is selected as the index of interest. Next, the graph drawing unit 65 sets the threshold values of the causal strength and the correlation coefficient (step S92). The threshold value may be determined from, for example, medical evidence or past data of the user him/herself. Alternatively, the threshold value may be set based on the dispersion of the causal strength or correlation coefficient of the index of interest and the other five indexes. Subsequently, the graph drawing unit 65 cuts off an arc (causal relationship) for which the value of the causal strength and/or coefficient is less than the threshold value set in step S92, and deletes the node of an index, unless the index is linked to "index 5: blood pressure" that is the index of interest (step S93).

By the above operation, a partial network relating to the index of interest (blood pressure), as shown in FIG. 10(*c*), is generated. In this example, "index 4: weight" and "index 2: exercise" are detected as factors influencing the blood pressure, and "index 6: healthcare cost" is detected as a factor influenced by the blood pressure. A solid arc shows a positive correlation, and a dashed arc a negative correlation. As additional information for each arc, information of the causal strength, the delay time, the correlation coefficient, or the like is shown.

In step S94, the support message generation unit 66 generates a support message relating to health management, based on information of the name, the causal strength, the delay time, the sign of correlation, or the like of each index extracted for the partial network. A template such as the following is prepared in the support message pattern storage unit 67.

Template Example:

T1: The <C> in <FC> seems to be influencing the <C> in <FT> the most.

T2: In your case, the <C> in <FC> seems to cause the <FT> to <C>, and it seems that the effect of the <FC> appears after <AD> days.

T3: The <FE> tends to <C> with the <C> in <FT>. Stay attentive.

A character string between "<" and ">" embedded within the template is replaced by a character string below upon generating the support message.

<FT>: Name of index of interest
<FE>: Name of index influenced by index of interest
<FC>: Name of index influencing index of interest
<C>: "increase" in the case of positive correlation or "decrease" in the case of negative correlation
<AD>: Value of delay time Delay In the case of the example in FIG. 10(*c*), the following support message is generated using templates T1 to T3.

"The increase in weight seems to be influencing the increase in blood pressure the most."

"In your case, the increase in exercise seems to cause the blood pressure to decrease, and it seems that the effect of the exercise appears after 3 days."

"The healthcare cost tends to increase with the increase in blood pressure. Stay attentive."

In step S95, the graph (FIG. 10(*c*)) of the partial network and the support message are displayed in the display device. By viewing such a support message, a user can easily grasp how the indexes relate to one another, for use in one's own health management.

Processing Example 2

Next, a specific example of data analysis processing and processing of generating and displaying support information that are executed by the health management support system 6 will be described. As a premise, it is assumed that a user has, over a certain period (e.g., one month or more), kept a record of a plurality of indexes such as the diet, number of steps, weight, blood pressure, and pulse rate, and that time series data and causal relationship data thereof are already accumulated in the data storing unit 62. An example will be described below in which processing of performing exercise support for a user, using time series data and causal relationship data of the number of steps and blood pressure for which a causal relationship has been found.

(1) Generation of Graph for User Support

Figure 11A:
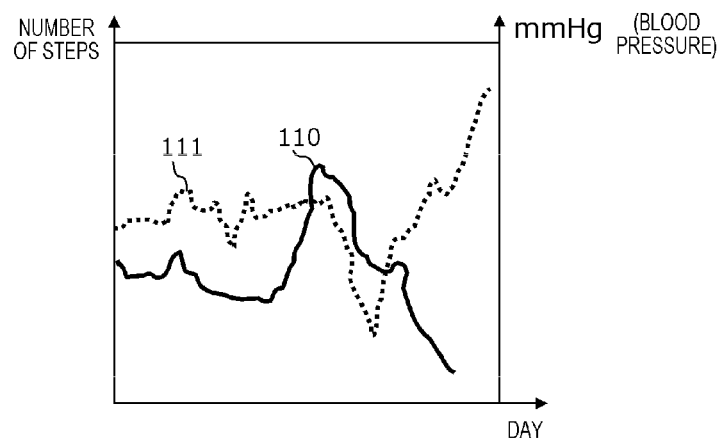
FIG. 11 Diagrams for illustrating processing of generating a graph for user support.
Figure 11B:
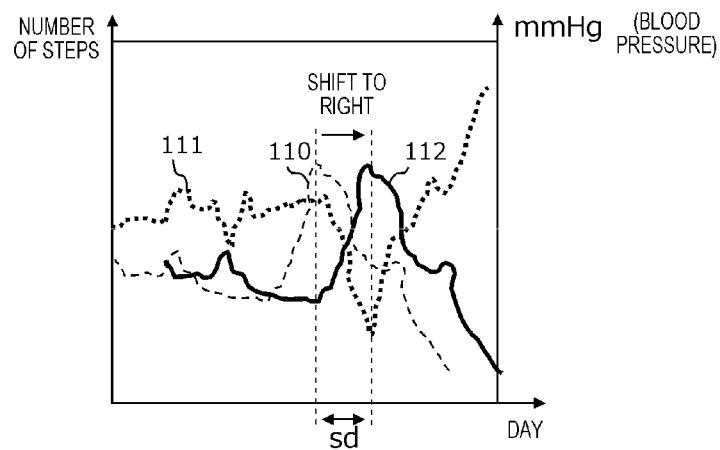

First, the graph drawing unit 65 creates a line graph in which the abscissa is time (in days) and the ordinate is the number of steps (in steps) and blood pressure (in mmHg), using time series data St(t) of the number of steps and time series data Bp(t) of the blood pressure. FIG. 11(*a*) is an example of the graph. Reference sign 110 denotes a graph line for the number of steps, and reference sign 111 denotes a graph line for the blood pressure.

Next, the graph drawing unit 65 acquires a time delay amount (delay time) sd between the number of steps and the blood pressure from the causal relationship data, and shifts the graph line 110 of the number of steps to the right by the time delay amount sd. (Alternatively, the graph line 111 of the blood pressure may be shifted to the left by sd.) FIG. 11(*b*) is an example of the graph after the shift, and reference sign 112 shows a graph line of the number of steps that has been shifted to the right by sd. Hereinafter, a graph in which one graph line has been shifted by the time delay amount sd, as shown in FIG. 11(*b*), is referred to as a "time-adjusted graph of the number of steps and blood pressure."

Figure 12:
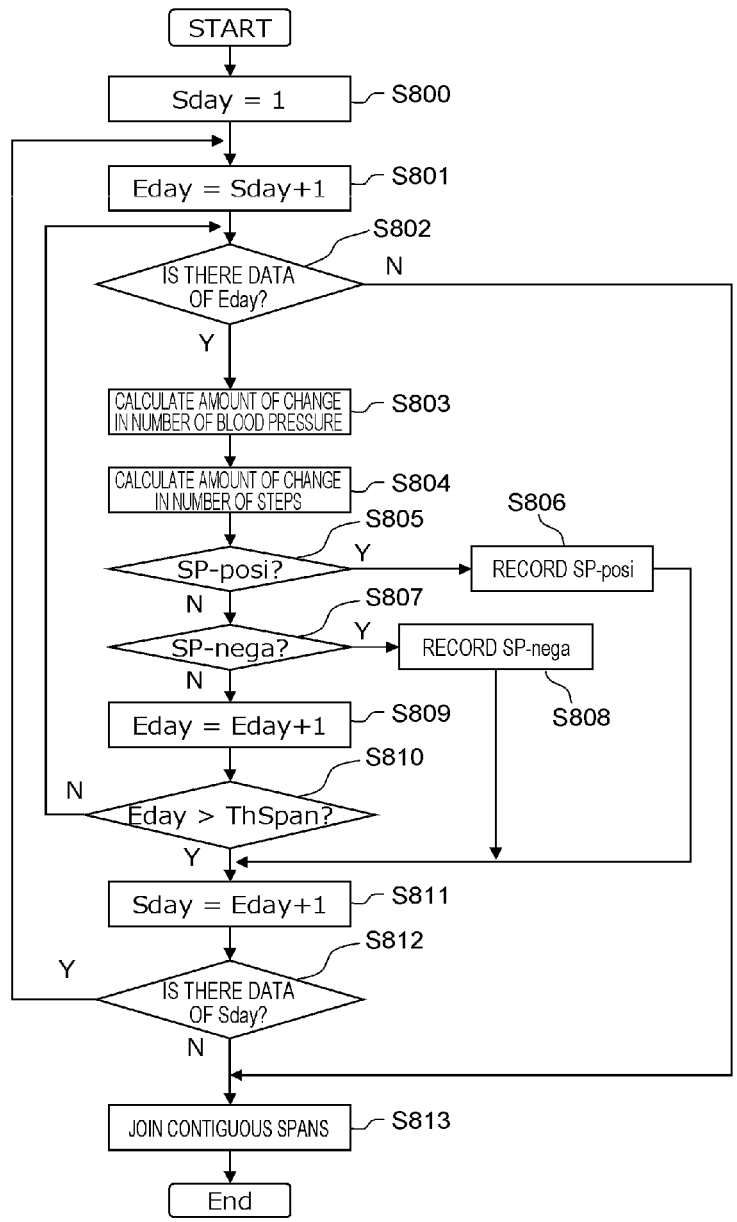
FIG. 12 A flowchart showing the flow of processing of detecting an exercise effect appearing span.

Subsequently, the graph drawing unit 65 detects a positive exercise effect appearing span SP-posi and a negative exercise effect appearing span SP-nega from the time-adjusted graph of the number of steps and blood pressure. Herein, the positive exercise effect appearing span refers to a span in the time-adjusted graph of the number of steps and blood pressure in which the number of steps increases and the blood pressure decreases. The negative exercise effect appearing span refers to a span in the same graph in which the number of steps decreases and the blood pressure increases. Various methods of detecting positive and negative exercise effect appearing spans are conceivable. An example is shown in FIG. 12.

In the description below, Sday and Eday are respectively variables showing the calculation starting day and the calculation ending day, and Db and Ds are respectively variables showing the amount of change in blood pressure and the amount of change in the number of steps. Bp(t) and St(t) respectively show the blood pressure and the number of steps in a particular day t. (Note that the number of steps St(t) is data that has been shifted by the time delay amount sd.) It is assumed that appropriate values are set in advance for the following threshold values.

ThSpan: Maximum period (e.g., 7 days) for calculating amount of change

ThDifBp: Difference value (positive value, e.g., 3 mmHg) by which blood pressure is determined to have increased/decreased ThDifSt: Difference value (positive value, e.g., 1000 steps) by which number of steps is determined to have increased/decreased When the processing in FIG. 12 is started, the graph drawing unit 65 assigns 1 to the calculation starting day Sday (step S800) and assigns Sday+1 to the calculation ending day Eday (step S801). It proceeds to step S803 if there is data of the number of steps and blood pressure for the calculation ending day Eday, or proceeds to step S813 if data of the number of steps and blood pressure is does not exist (step S802).

In steps S803 and S804, the graph drawing unit 65 calculates the amount of change Db in blood pressure and the amount of change Ds in the number of steps between the calculation starting day Sday and the calculation ending day Eday with the following equations.

$$Db = Bp(Eday) - Bp(Sday)$$

$$Ds = St(Eday) - St(Sday)$$

Subsequently, determination on the positive exercise effect appearing span SP-posi is performed (step S805). Specifically, in the case where the amount of change Db in blood pressure satisfies the condition "Db<−1×ThDifBp" and the amount of change Ds in the number of steps satisfies the condition "Ds>ThDifSt" (YES in step S805), the graph drawing unit 65 records a span from Sday to Eday as SP-posi (step S806) and proceeds to step S811. In the case where Db or Ds does not satisfy the above condition (NO in step S805), it is determined that a positive exercise effect has not appeared and proceeds to step S807.

In step S807, determination on the negative exercise effect appearing span SP-nega is performed. Specifically, in the case where the amount of change Db in blood pressure satisfies the condition "Db>ThDifBp" and the amount of change Ds in the number of steps satisfies the condition "Ds<−1×ThDifSt" (YES in step S807), the graph drawing unit 65 records the span from Sday to Eday as SP-nega (step S808) and proceeds to step S811. In the case where Db or Ds does not satisfy the above condition (NO in step S807), it is determined that a negative exercise effect has not appeared and proceeds to step S809.

Then, Eday is incremented by 1 (step S809), and processing of steps S802 to S809 is repeated until Eday reaches ThSpan (step S810). That is, determination on whether the exercise effect appearing span applies is performed sequentially, while the length of the span (1 day being the shortest and ThSpan being the longest) is increased by 1 day at a time. Accordingly, not only day-to-day changes in the number of steps and blood pressure, but also the trend of change on a macro level within, to some extent, a long period can be assessed. Therefore, failures to detect an exercise effect appearing span can be reduced. Using FIG. 13, an example of detecting an exercise effect appearing span by varying the length of the span will be described.

Figure 13:
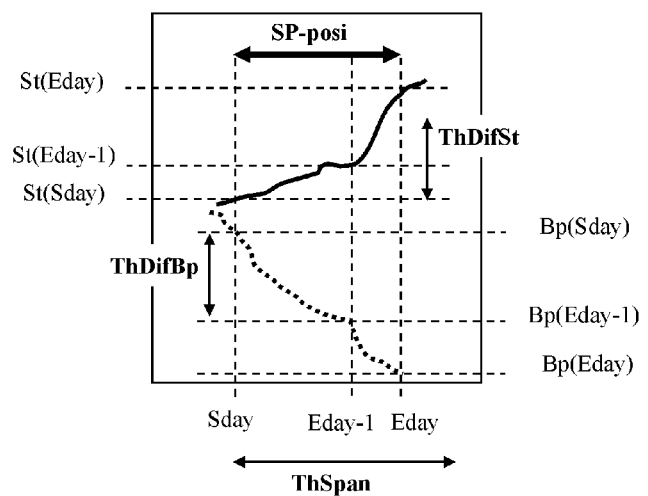
FIG. 13 A diagram showing an example of detecting a positive exercise effect appearing span SP-posi.

FIG. 13 is an example of detecting the positive exercise effect appearing span SP-posi. In FIG. 13, there is an increasing trend for the number of steps St(t), and there is a decreasing trend for the blood pressure Bp(t). The span "Sday to (Eday−1)" is not determined as Sp-posi, since the amount of change Ds in the number of steps that equals St(Eday−1)−St(Sday) does not satisfy the condition Ds>ThDifSt. However, the span "Sday to Eday" is detected as the positive exercise effect appearing span SP-posi, since, in subsequent determination processing for the span "Sday to Eday," the amount of change Db in blood pressure that equals Bp(Eday−1)−Bp(Sday) satisfies the condition "Db<−1×ThDifBp" and the amount of change Ds in the number of steps that equals St(Eday)−St(Sday) satisfies the condition "Ds>ThDifSt."

In the above manner, when the determination processing for spans starting from the calculation starting day Sday has ended, the graph drawing unit 65 updates the calculation starting day Sday with Sday=Eday+1 (step S811). It returns to step S801 to repeat the processing if data of the number of steps and blood pressure for Sday after the update exists, or it proceeds to step S813 if data of the number of steps and blood pressure does not exist (step S812).

Figure 14:
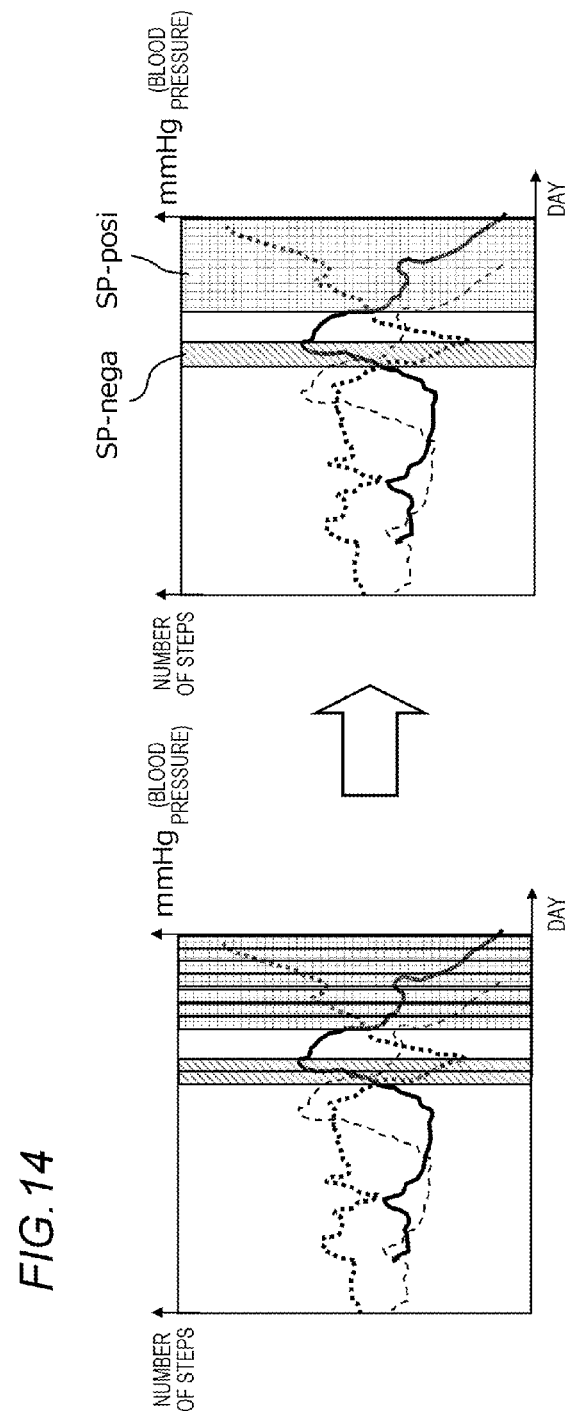
FIG. 14 A diagram showing an example of joining contiguous spans.

In step S813, the graph drawing unit 65 performs, if a plurality of detected exercise effect appearing spans include contiguous spans, processing of joining the contiguous spans. At this time, the positive exercise effect appearing span SP-posi and the negative exercise effect appearing span SP-nega are not joined. FIG. 14 shows an example of joining contiguous spans. A graph on the left side in FIG. 14 shows SP-posi and SP-nega that have been detected, and a graph on the right side shows SP-posi and SP-nega with contiguous spans joined. Only spans adjacent without an interval may be joined, or spans between which an interval is extremely short (e.g., approximately one to several days) may be regarded contiguous spans and also joined.

Figure 15:
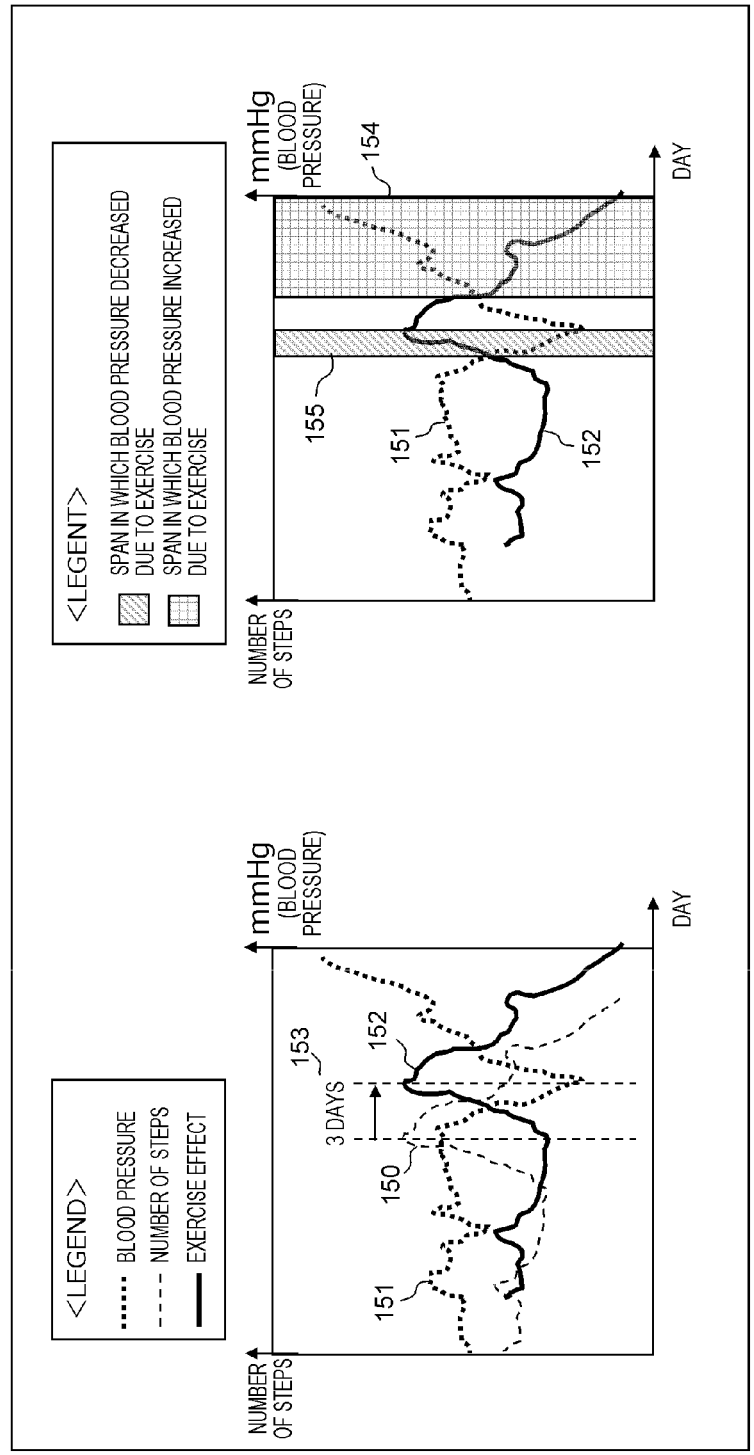
FIG. 15 A diagram showing an example of the graph for user support.

Based on information obtained through the processing described above, the graph drawing unit 65 generates a graph for user support to be presented to a user. FIG. 15 is an example of the graph for user support. In this example, two graphs are displayed. Drawn in the graph on the left side are, in addition to a number-of-steps graph line 150 plotted for time series data of the number of steps and a blood pressure graph line 151 plotted for time series data of the blood pressure, an exercise effect graph line 152 plotted by shifting the number-of-steps graph line 150 by a time delay amount and information 153 showing the time delay amount (3 days in this example). Drawn in the graph on the right side are a positive exercise effect appearing span 154 and a negative exercise effect appearing span 155 on the blood pressure graph line 151 and the exercise effect graph line 152. While it is possible that a plurality of exercise effect appearing spans exist, all may be drawn on the graph, or only a representative one (e.g., one in which the span is longest) may be drawn on the graph. A caption for each element can be set at will.

(2) Generation of Message for User Support

As an example, this embodiment presents two types of messages for user support of a first message including a result of assessment of an exercise carried out by a user and/or an advise for the future and a second message including the delay characteristics (time delay amount) of the exercise effect for the user.

Figure 16:
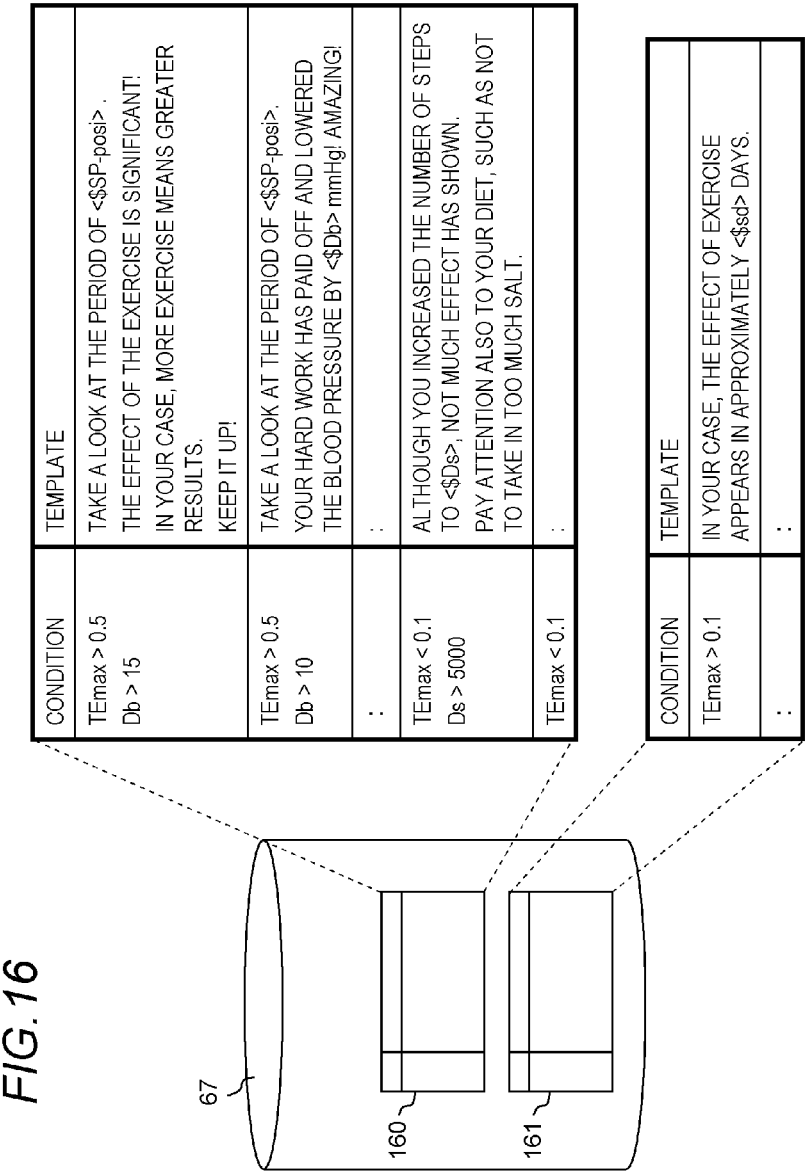
FIG. 16 An example of templates stored in a support message pattern storage unit.

FIG. 16 shows an example of a template stored in the support message pattern storage unit 67. The support message pattern storage unit 67 includes a first table 160 in which a plurality of templates for the first message are registered and a second table 161 in which a plurality of templates for the second message are registered. The templates may be registered in advance in the system, or a system administrator or user may be able to add, edit, or delete the template. Each template is registered in association with a selection condition for the template. It is advisable to set the selection condition using a value such as, for example, a causal strength TEmax, number of steps St, a blood pressure Bp, the amount of change Ds in the number of steps, the amount of change Db in blood pressure, or the time delay amount sd. In the example of FIG. 16, a selection condition combining the condition of the causal strength TEmax and the condition of the amount of change Ds in the number of steps or amount of change Db in blood pressure is set in the template for the first message, and a selection condition with the causal strength TEmax is set in the template for the second message. A character string between "<$" and ">" embedded within the template is a portion to be replaced by an actual value upon generating the message for user support.

For example, consider a case where the following are obtained.

SP-posi: Feb. 5, 2013 to Feb. 12, 2013
TEmax: 0.53
sd: 3
Db: 14
Ds: 2050

The support message generation unit 66 selects a second template from the first table 120 to generate the first message saying "Take a look at the period of Feb. 5, 2013 to Feb. 12, 2013. Your hard work has paid off and lowered the blood pressure by 14 mmHg! Amazing!"
and selects a first template from the second table 121 to generate the second message saying "In your case, the effect of exercise appears in approximately three days."

Figure 17:
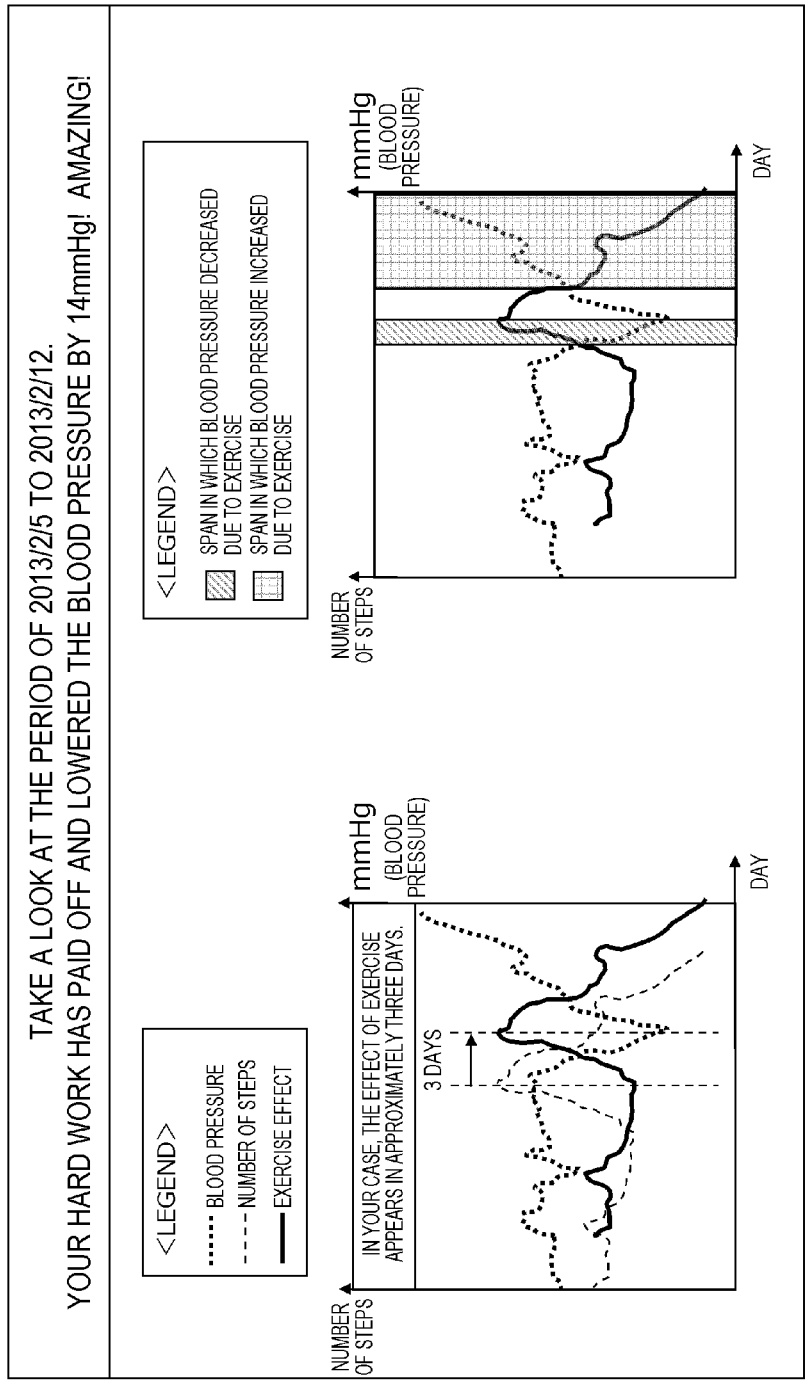
FIG. 17 A display example of support information provided to a user.

The generated message for user support is synthesized in a predetermined area of the graph for user support by the drawing synthesis unit 68 and output to a display device, an external terminal, or the like by the output unit 69. FIG. 17 is a display example of the support information. The first message is displayed in the upper portion of a screen, and the second message is displayed in the upper portion of the left graph. By viewing such support information, a user can become aware of the delay characteristics in the effect of one's own exercise and check the effect resulting from the exercise intuitively and with confidence.

The system described above enables a health management support in consideration of a time delay until an effect resulting from an exercise appears. Particularly, since the causal strength and delay time calculated from data of the number of steps and blood pressure of a user him/herself are used, it is possible to present a causal relationship of an exercise carried out by the user and an effect thereof in a comprehensible manner, so that the motivation to continue the exercise is maintained.

By viewing the screen in FIG. 17, one can become aware of his/her inherent physiological characteristics that an effect resulting from an exercise appears with a delay of approximately 3 days. Thus, a user can understand which parts of the increase or decrease in the number of steps and the change in blood pressure to compare, and can check the outcomes of past exercises or conversely notice the blood pressure worsening due to inactivity. Also, health management (e.g., an exercise plan or goal setting for the number of steps or blood pressure) in consideration of one's own physiological characteristics is made possible.

By comparing the exercise effect graph line (shifted number-of-steps graph line) and the blood pressure graph line in the screen of FIG. 17, the causal relationship (negative correlation) of the increase or decrease in the number of steps and the change in blood pressure can be understood intuitively. Further, through displaying of the positive exercise effect appearing span SP-posi, it can be easily grasped that the increase in the number of steps (past effort) relates directly to the positive change in blood pressure (i.e., drop in blood pressure). Therefore, one can be motivated to carry out and continue the exercise. In addition, through displaying of the negative exercise effect appearing span SP-nega, it can also be easily grasped that the decrease in the number of steps (past inactivity) relates directly to the negative change in blood pressure (i.e., rise in blood pressure). This has an effect of encouraging the user to rethink and be reminded of the necessity to continue carrying out the exercise.

The configuration of the embodiment described above merely shows one specific example of the present invention and is not intended to limit the scope of the present invention. The present invention may, without departing from the technical idea thereof, employ various specific configurations. In the above embodiment, a correlation coefficient in linear regression has been used as the correlation information between a cause index and an effect index. However, a correlation between two indexes may be assessed by other methods. For example, in the case where two indexes X and Y lack a linear relationship, but are in a relationship such that fitting with a non-linear equation is possible, there can be a simplification into a linear problem through conversion of one of the indexes to assess the correlation coefficient of the two indexes in the same manner. For example, a regression analysis method such logistic regression can be suitably used.

REFERENCE SIGNS LIST

1 Causal network generation system 1
10 Time series data acquisition unit
11 Causal relationship evaluation unit
12 Causal relationship data output unit
6 Health management support system
60 Indicator recording unit
61 Data transmission unit
62 Data storing unit
63 Causal network generation unit
64 Data acquisition unit
65 Graph drawing unit
66 Support message generation unit
67 Support message pattern storage unit
68 Drawing synthesis unit
69 Output unit
70 Device
71 Pedometer
72 Blood pressure meter
80 Online storage
81 Terminal
82 Cloud server
83 Terminal

The invention claimed is:

1. A causal network generation system to generate a causal network representing a causal relationship between a plurality of events that occur to a target, the causal network generation system comprising a processor configured with a program to perform operations comprising:
   operation as a data acquisition unit that acquires time series data of each of a plurality of indexes used for quantitatively describing the plurality of events;
   operation as a causal relationship evaluation unit that evaluates, for each pair of two different indexes selected from the plurality of indexes, a causal relationship between the two indexes; and
   operation an output unit that outputs data describing a causal relationship for each pair of the two indexes evaluated by the causal relationship evaluation unit,
   wherein the processor is configured to perform operations such that:
   operation as the causal relationship evaluation unit comprises operation as the causal relationship evaluation unit that assumes one of the two indexes as a cause index and the other as an effect index, and calculating a causal strength between a change in the cause index and a change in the effect index after a time s while varying a value of the time s to evaluate a causal strength between the cause index and the effect index and a delay time for propagation of an influence of the cause index to the effect index,
   operation as the causal relationship evaluation unit comprises operation as the causal relationship evaluation unit that calculates, as the causal strength, a transfer entropy $TE_{XY}(s)$ defined by an equation:

$$TE_{XY}(s) = \left[\log_2 \frac{P(y(t+s), y(t), x(t)) \cdot P(y(t))}{P(y(t), x(t)) \cdot P(y(t+s), y(t))}\right]$$

where
- t: time,
- s: delay time,
- x(t): time series data of the cause index,
- y(t): time series data of the effect index,
- P( ): probability density function, and
- [*]: time average of *.

2. The causal network generation system according to claim 1, wherein
the processor is configured with the program to perform operations such that operation as the causal relationship evaluation unit comprises operation as the causal relationship evaluation unit that evaluates a delay time with which the causal strength between the cause index and the effect index becomes maximum, and
the causal relationship output from the output unit includes information of the delay time with which the causal strength between the cause index and the effect index becomes maximum and information of a maximum causal strength between the cause index and the effect index.

3. The causal network generation system according to claim 1, wherein
the processor is configured with the program to perform operations such that operation as the causal relationship evaluation unit comprises operation as the causal relationship evaluation unit that evaluates the causal strength between the cause index and the effect index for n delay times from first to n-th (where n is an integer greater than or equal to 2), and
the causal relationship output from the output unit includes information of n delay times from first to n-th and information of n causal strengths corresponding to the respective first to n-th delay times.

4. The causal network generation system according to claim 1, wherein
the processor is configured with the program to perform operations such that operation as the causal relationship evaluation unit comprises operation as the causal relationship evaluation unit that calculates a correlation coefficient between a value of the cause index and a value of the effect index after the delay time, and
the causal relationship output from the output unit includes information of the correlation coefficient.

\* \* \* \* \*